US008398579B2

(12) United States Patent
Morris et al.

(10) Patent No.: US 8,398,579 B2
(45) Date of Patent: Mar. 19, 2013

(54) CATHETER INCLUDING COMPOSITE GUIDE AND METHODS FOR USE OF THE SAME

(75) Inventors: David B. Morris, Anoka, MN (US);
Eric J. Thor, Arden Hills, MN (US);
Michael J. Bonnette, Minneapolis, MN (US); Jason M. Bronstad, St. Francis, MN (US); Corey Rasch, Stillwater, MN (US); Brian D. Bruckner, Maple Grove, MN (US); Jason Anderson, Minnetonka, MN (US); Laszlo T. Farago, Hudson, WI (US); Diana Dutcher, Maple Grove, MN (US)

(73) Assignee: Medrad, Inc., Indianola, PA (US)

( * ) Notice: Subject to any disclaimer, the term of this patent is extended or adjusted under 35 U.S.C. 154(b) by 0 days.

(21) Appl. No.: 12/968,853

(22) Filed: Dec. 15, 2010

(65) Prior Publication Data

US 2011/0152908 A1 Jun. 23, 2011

Related U.S. Application Data

(60) Provisional application No. 61/286,849, filed on Dec. 16, 2009.

(51) Int. Cl.
*A61B 17/20* (2006.01)
*A61B 17/22* (2006.01)

(52) U.S. Cl. ............................... 604/22; 606/159

(58) Field of Classification Search .................. 606/159, 606/169, 170, 171, 180; 604/22, 115–117, 604/175, 149, 131, 132, 141, 140, 523–539, 604/284, 264
See application file for complete search history.

(56) References Cited

U.S. PATENT DOCUMENTS

| 1,902,418 | A | 3/1933 | Pilgrim |
| 3,930,505 | A | 1/1976 | Wallach |
| 4,631,052 | A | 12/1986 | Kensey |
| 4,690,672 | A | 9/1987 | Veltrup |
| 4,790,813 | A | 12/1988 | Kensey |
| 4,883,459 | A | 11/1989 | Calderon |
| 4,898,574 | A | 2/1990 | Uchiyama et al. |
| 4,913,698 | A | 4/1990 | Ito et al. |
| 4,950,238 | A | 8/1990 | Sullivan |
| 5,086,842 | A | 2/1992 | Cholet |
| 5,135,482 | A | 8/1992 | Neracher |
| 5,273,526 | A | 12/1993 | Dance et al. |

(Continued)

FOREIGN PATENT DOCUMENTS

| WO | 03000316 A1 | 1/2003 |
| WO | 2005099802 A2 | 10/2005 |

OTHER PUBLICATIONS

European Search Report from related European Application, dated Oct. 7, 2011.

*Primary Examiner* — Tuan V Nguyen
(74) *Attorney, Agent, or Firm* — David Schramm

(57) ABSTRACT

A catheter including a catheter body having a catheter lumen is disclosed. A manifold assembly is coupled with a proximal catheter portion. A manifold lumen extends through the manifold assembly and includes an assembly cavity extending around the proximal catheter portion. A fluid jet loop including fluid jet orfices along a tapered loop guide surface is coupled with a distal catheter portion. The catheter further includes a composite guide having a proximal guide insert and a distal guide. The proximal guide insert is positioned within the assembly cavity and includes a guide insert surface flush with a catheter body interior wall. The distal guide includes a tapered loop guide surface, and an intermediate guide surface of the catheter lumen is flushly engaged with a leading edge of the tapered loop guide surface, the distal guide continuously tapering inwardly and distally along the tapered loop guide surface.

8 Claims, 11 Drawing Sheets

U.S. PATENT DOCUMENTS

| | | |
|---|---|---|
| 5,318,518 A | 6/1994 | Plechinger et al. |
| 5,496,267 A | 3/1996 | Drasler et al. |
| 5,569,184 A | 10/1996 | Crocker et al. |
| 5,569,199 A | 10/1996 | Solar |
| 5,687,714 A | 11/1997 | Kolobow et al. |
| 5,713,849 A | 2/1998 | Bosma et al. |
| 5,928,186 A | 7/1999 | Homsma et al. |
| 5,964,223 A | 10/1999 | Baran |
| 5,989,281 A | 11/1999 | Barbut et al. |
| 6,096,001 A | 8/2000 | Drasler et al. |
| 6,117,510 A | 9/2000 | Ishikawa et al. |
| 6,128,799 A | 10/2000 | Nagata et al. |
| 6,129,697 A | 10/2000 | Drasler et al. |
| 6,135,977 A | 10/2000 | Drasler et al. |
| 6,221,049 B1 | 4/2001 | Selmon et al. |
| 6,231,546 B1 | 5/2001 | Milo et al. |
| 6,235,000 B1 | 5/2001 | Milo et al. |
| 6,258,061 B1 | 7/2001 | Drasler et al. |
| 6,436,090 B1 | 8/2002 | Sanchez et al. |
| 6,471,683 B2 | 10/2002 | Drasler et al. |
| 6,514,217 B1 | 2/2003 | Selmon et al. |
| 6,544,218 B1 | 4/2003 | Choi |
| 6,676,627 B1 | 1/2004 | Bonnette et al. |
| 6,755,803 B1 | 6/2004 | Le et al. |
| 6,805,684 B2 | 10/2004 | Bonnette et al. |
| 6,875,193 B1 | 4/2005 | Weisel et al. |
| 6,984,239 B1 | 1/2006 | Drasler et al. |
| 7,037,290 B2 * | 5/2006 | Gardeski et al. ........... 604/95.01 |
| 7,220,269 B1 | 5/2007 | Ansel et al. |
| 7,285,119 B2 | 10/2007 | Stewart et al. |
| 7,326,208 B2 | 2/2008 | Vanney et al. |
| 7,381,200 B2 | 6/2008 | Katoh et al. |
| 7,842,010 B2 | 11/2010 | Bonnette et al. |
| 7,879,022 B2 | 2/2011 | Bonnette et al. |
| 8,012,117 B2 | 9/2011 | Bonnette et al. |
| 2001/0047149 A1 | 11/2001 | Traxler et al. |
| 2005/0049609 A1 | 3/2005 | Gunderson et al. |
| 2006/0129091 A1 | 6/2006 | Bonnette et al. |
| 2007/0010763 A1 | 1/2007 | Lentz et al. |
| 2008/0300532 A1 | 12/2008 | Bonnette et al. |
| 2009/0024071 A1 | 1/2009 | Yeung et al. |

* cited by examiner

800 ↘

802 — FEEDING AN INSTRUMENT INTO THE CATHETER, THE CATHETER INCLUDES A MANIFOLD ASSEMBLY COUPLED WITH A CATHETER BODY AT A PROXIMAL CATHETER PORTION, A CATHETER LUMEN EXTENDS THROUGH THE CATHETER FROM THE PROXIMAL CATHETER PORTION TO A DISTAL CATHETER PORTION, AND AN ASSEMBLY CAVITY EXTENDS AROUND THE PROXIMAL CATHETER PORTION

↓

804 — FEEDING THE INSTRUMENT THROUGH AT LEAST A CATHETER LUMEN AND A FLUID JET LOOP, AND THE INSTRUMENT IS FED INTO AND THROUGH THE CATHETER LUMEN BY WAY OF A COMPOSITE GUIDE SURFACE, WHEREIN FEEDING THE INSTRUMENT INCLUDES:

↓

806 — GUIDING THE INSTRUMENT INTO A CATHETER LUMEN THROUGH A GUIDE INSERT FILLING THE ASSEMBLY CAVITY, AND THE INSTRUMENT IS GUIDED ALONG A GUIDE INSERT SURFACE IN THE PROXIMAL GUIDE INSERT FLUSH WITH A CATHETER BODY INTERIOR WALL

↓

808 — GUIDING THE INSTRUMENT ALONG A DISTAL GUIDE NEAR THE DISTAL CATHETER PORTION, WHEREIN THE DISTAL GUIDE INCLUDES AN INTERMEDIATE GUIDE SURFACE AND A TAPERED GUIDE SURFACE OF THE FLUID JET LOOP, AND THE TAPERED GUIDE SURFACE INCLUDES FLUID JET ORIFICES DIRECTED TOWARD THE PROXIMAL CATHETER PORTION, AND THE INSTRUMENT IS GUIDED ALONG THE INTERMEDIATE GUIDE SURFACE OF THE CATHETER LUMEN FLUSHLY ENGAGED WITH A LEADING EDGE OF THE TAPERED GUIDE SURFACE

*FIG. 8* ized to slidably 25
CATHETER INCLUDING COMPOSITE GUIDE AND METHODS FOR USE OF THE SAME

CROSS-REFERENCE TO RELATED APPLICATIONS

This application is a non-provisional of U.S. Application No. 61/286,849 filed Dec. 16, 2009, the contents of which are incorporated herein by reference.

TECHNICAL FIELD

Catheters and guiding of instruments through catheters.

BACKGROUND

To guide a catheter to a desired treatment site introducers and guide wires are used. In the case of guide wires, the guide wire is positioned within the vessel near the treatment site and the catheter is fed over the guide wire. The catheter follows the path of the guide wire through the vasculature until a portion of the catheter, such as the distal tip, reaches the treatment site. In some examples, the catheter includes a dedicated guide wire lumen sized and shaped to slidably receive the guide wire. The guide wire lumen may be entirely isolated from the other features of the catheter, including instrument lumens, instruments and the like. The provision of the guide wire lumen requires an allotment of space in the catheter to accommodate a guide wire. Alternatively, the catheter can be made larger to accommodate both the guide wire lumen and the desired instruments and instrument lumens. Larger catheters can have difficulty navigating the tortuous vasculature of the body and in some cases are unable to reach a treatment site in smaller vessels because they are simply too large to fit within the vessels.

In other examples, the guide wire is fed through an instrument or delivery lumen thereby consolidating the functions of a guide wire lumen and an instrument lumen into a single passage. In many examples, instruments, tubes and the like are positioned within instrument lumens that provide a discontinuous surface related to the function or construction of the catheter. These discontinuous surfaces snag guide wires that are fed into the instrument lumens preventing further advancement of the guide wires. This difficulty is further aggravated with guide wires having curved features designed to navigate bends in the vasculature. The curved features easily catch on the discontinuous surfaces of the instrument lumen and interrupt the smooth delivery of the instrument through the catheter. Stated another way, the interruptions in the consolidated lumen easily snag and halt the desired advancement of a curved guide wire. Because of these difficulties, a solution is needed for smoother transport of guide wires and the like inside of catheters.

BRIEF DESCRIPTION OF THE DRAWINGS

FIG. 8 is a block diagram showing one example of a method for using a thrombectomy catheter having a composite guide.

DESCRIPTION OF THE EMBODIMENTS

In the following detailed description, reference is made to the accompanying drawings which form a part hereof, and show, by way of illustration, specific embodiments in which the device of the present disclosure may be practiced. These embodiments are described in sufficient detail to enable those skilled in the art to practice the teachings of the present disclosure, and it is to be understood that other embodiments may be utilized and that structural changes may be made without departing from the scope of the present disclosure. Therefore, the following detailed description is not to be taken in a limiting sense, and the scope of the present disclosure is defined by the appended claims and their equivalents.

Figure 1:
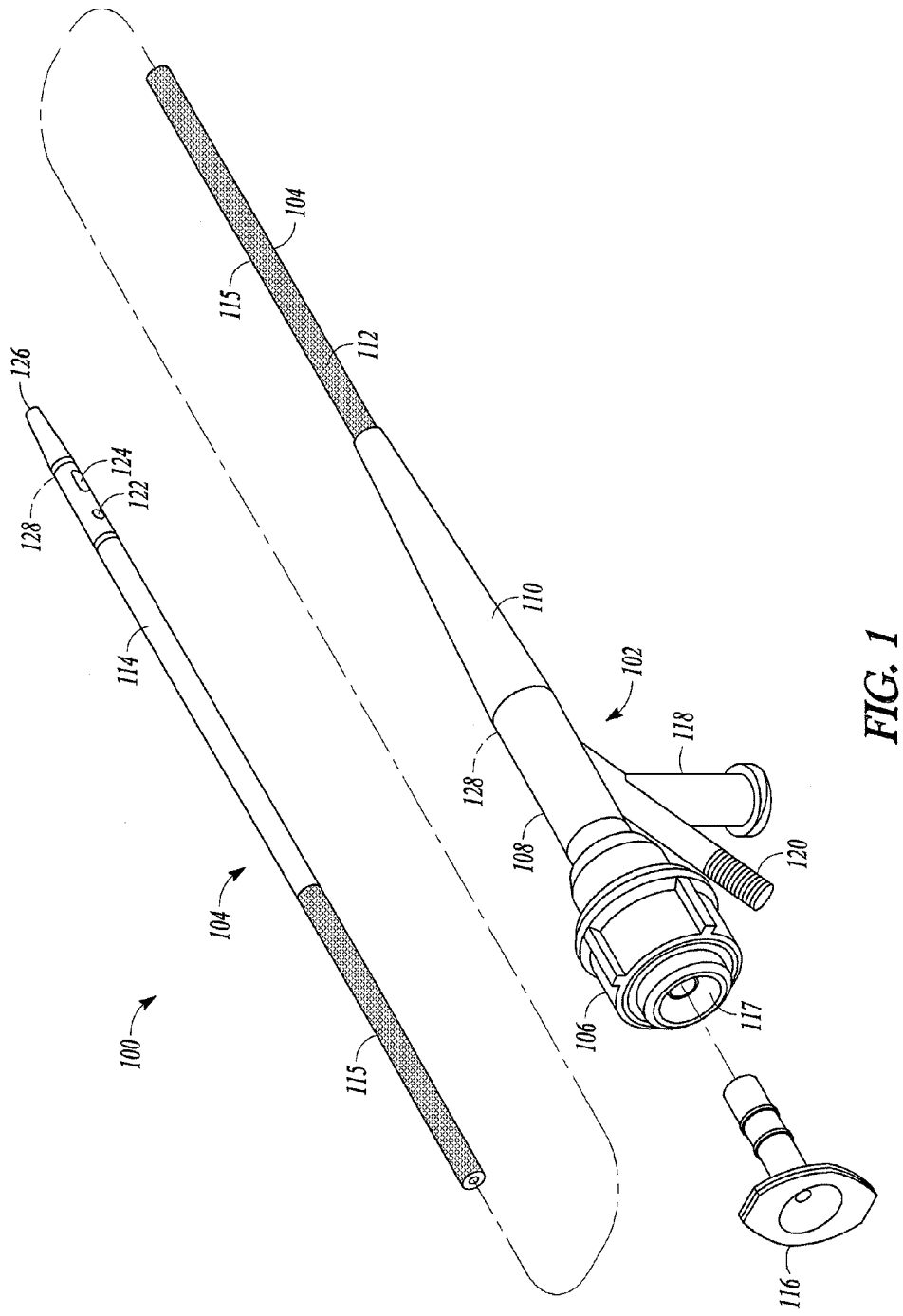
FIG. 1 is a perspective view of one example of a thrombectomy catheter

One example of a thrombectomy catheter 100 is shown in FIG. 1. The thrombectomy catheter 100 includes a catheter body 104 and a manifold assembly 102. The manifold assembly 102 includes a manifold proximal portion 106 and a manifold distal portion 108. A exhaust tube 120 extends into the manifold assembly 102. As shown in FIG. 1, in one example, the exhaust tube receives an injection port 118 and thereafter extends into the manifold assembly 102 where it meets with a manifold lumen shown in later figures. An introducer 116 is received in the manifold proximal portion 106. Referring again to FIG. 1, the introducer 116 is received within an introducer lumen 117 in the manifold proximal portion 106. The introducer lumen 117 and the lumen within the introducer 116 are in communication with the manifold lumen and a catheter lumen extending through the catheter body 104.

The catheter body 104 extends away from the manifold assembly 102. As shown in FIG. 1, a strain relief fitting 110 is coupled between the catheter body 104 at the catheter proximal portion 112 and the manifold assembly 102 at the manifold distal portion 108. The catheter body 104 extends away from the manifold assembly 102 toward a catheter distal portion 114. In one example, the catheter body 104 includes a catheter support, such as a braided catheter support 115. Referring to FIG. 1, the braided catheter support 115 is shown in a partial cutaway view with cross hatching. Optionally, the braided catheter support 115 extends through a portion of the catheter body 104. In yet another option, the braided catheter support 115 extends throughout the catheter body 104.

The catheter distal portion 114 includes one or more outflow orifices 122 and one or more inflow orifices 124. As described in further detail below the inflow and outflow orifices 124, 122 cooperate with fluid jets to provide a cross stream effect wherein fluid is projected from the catheter body 104 through the outflow orifice 122 and returns to the catheter body 104 through the inflow orifice 124. The fluid entering and exiting the catheter body 104 thereby develops a circular or cross stream flow that is able to engage with thrombus material within a vessel, break up the thrombus material and draw the thrombus particles into the catheter body 104. The catheter distal portion 114 further includes a guide wire orifice 126. The guide wire orifice 126 is sized and shaped to receive and pass through a guide wire extending within the catheter 100, for instance, a guide wire extending through the introducer 116, a manifold lumen within the manifold assembly 102, the catheter body 104 and finally through the guide wire orifice 126. In one option, a guide wire is back loaded into the catheter 100. For example, the guide wire is back loaded through the introducer 116, into the catheter body 104 and out of the guide wire orifice 126 and into the vasculature. In another option, the catheter 100 is fed over a guide wire fed first through the guide wire orifice 126 and through at least a portion of the catheter body 104 (e.g., an over the wire or rapid exchange catheter).

Figure 2:
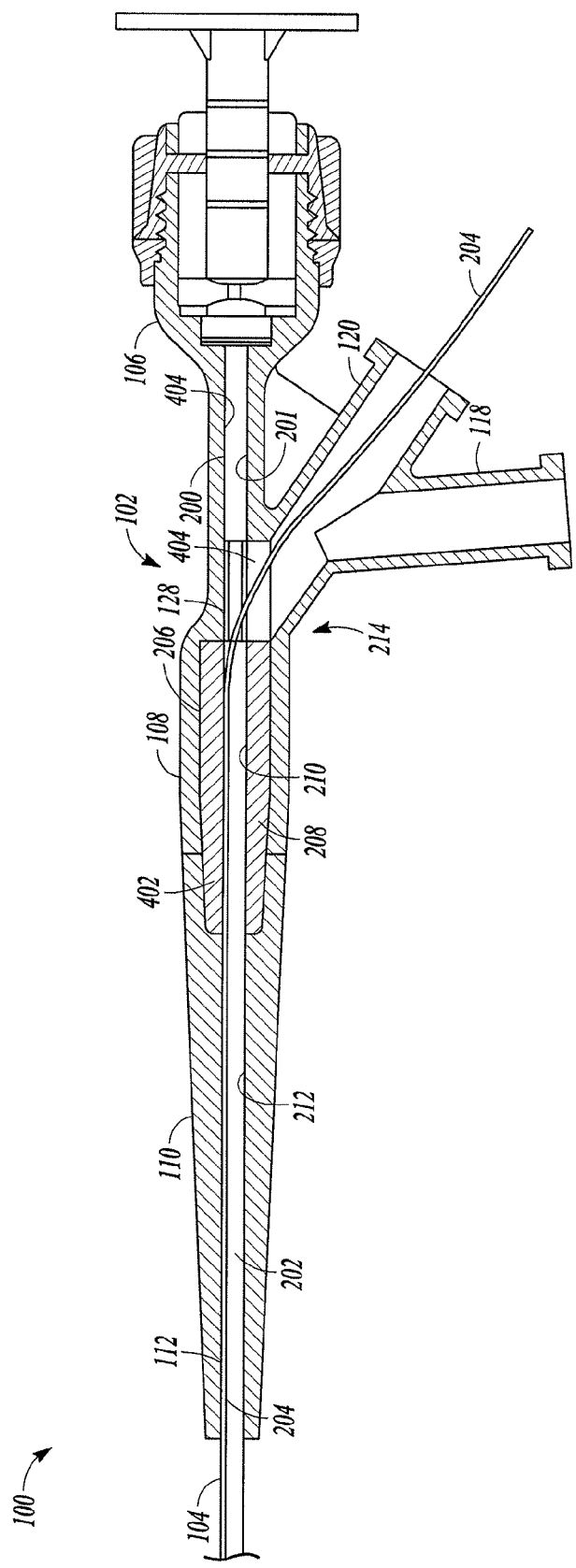
FIG. 2 is a cross-sectional view of one example of the manifold assembly including an example guide insert of a composite guide.

FIG. 2 shows the manifold assembly 102 in a cross sectional view. A manifold lumen 200 extends through the manifold assembly 102 from the manifold proximal portion 106 to the manifold distal portion 108. As shown in FIG. 2, the catheter lumen 202 is in communication with the manifold lumen 200. The catheter body 104 is coupled with the manifold assembly 102 with the strain relief fitting 110 previously shown in FIG. 1. The strain relief fitting 110 is shown in FIG. 2 extending around the catheter body 104 and engaged with the manifold assembly 102.

As previously discussed, the exhaust tube 120 and the injection port 118 are in communication with one another and also in communication with the manifold lumen 200. A high pressure tube 204 such as a stainless steel hypo tube extends through the exhaust tube 120 and into the manifold lumen 200 where the high pressure tube 204 continues to extend through the catheter lumen 202 toward the catheter distal portion 114 shown in FIG. 1.

As shown herein the thrombectomy catheter 100 includes a composite guide 128 having at least a first guide portion 214 (shown in FIG. 2) near the manifold assembly 102 and a second guide portion 311 (described below and shown in FIGS. 3A, B) near the catheter distal portion 114. The composite guide 128 directs guide wires, flow wires or other instruments through the lumens of manifold assembly 102 and catheter body 104 used to perform a thrombectomy procedure. Snagging of an instrument, such as a guide wire, within the thrombectomy catheter 100 is therefore minimized by the composite guide 128. It will be understood by those of skill in the art that any diagnostic or therapeutic instrument that can be delivered through a catheter could benefit from the composite guide of the present disclosure.

Referring to FIG. 2, the first guide portion 214 includes a guide insert 208 that provides a smooth transition between the manifold assembly 102 and the catheter body 104. In one example, the guide insert 208 is constructed with, but not limited to, metals, plastics and the like. The guide insert 208 is formed by one or more of molding, machining, casting, and the like. The first guide portion 214 including the guide insert 208 is positioned within an assembly cavity 206 of the manifold assembly 102. The assembly cavity 206 shown in FIG. 2 facilitates construction of the catheter 100. For instance, the catheter components are fed through the exhaust tube 120 and into the assembly cavity 206 before being fed into the catheter body 104 toward the catheter distal portion 114. Once the components of the catheter 100 are assembled the guide insert 208, in one example, is fed down the exterior of the catheter body 104 and into engagement with the manifold assembly 102. The guide insert fills the assembly cavity 206. The guide insert surface 210 is flush with a catheter body interior wall 212 of the catheter body 104 and a manifold interior wall 201. The guide insert surface 210 cooperates with the catheter body interior wall 212 and the manifold interior wall 201 to form the first guide portion 214.

Figure 3A:
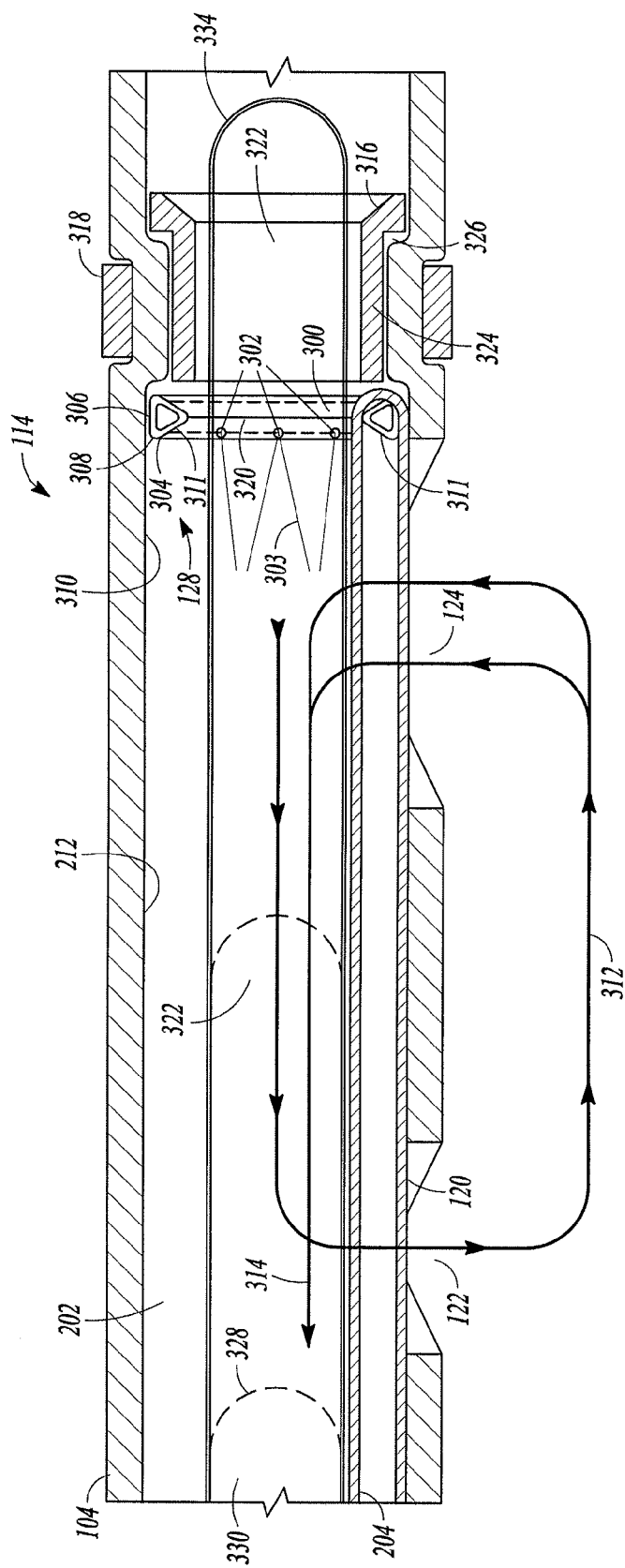
FIG. 3A is a cross-sectional view of one example of a distal catheter portion including an example fluid jet loop having a tapered guide surface of the composite guide.
Figure 3B:
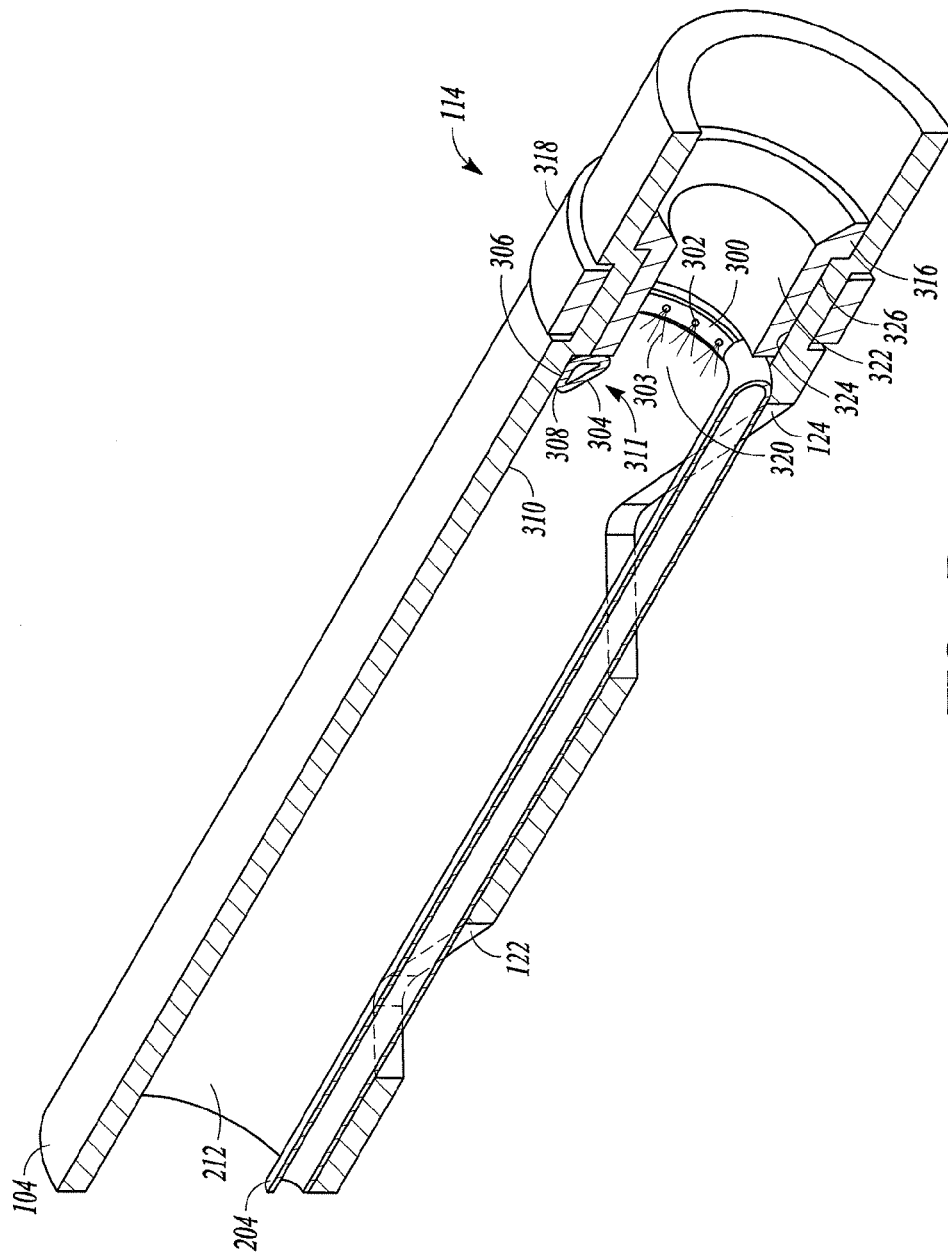
FIG. 3B is a sectional perspective view of the distal catheter portion including the fluid jet loop shown in FIG. 3A.
Figure 3C:
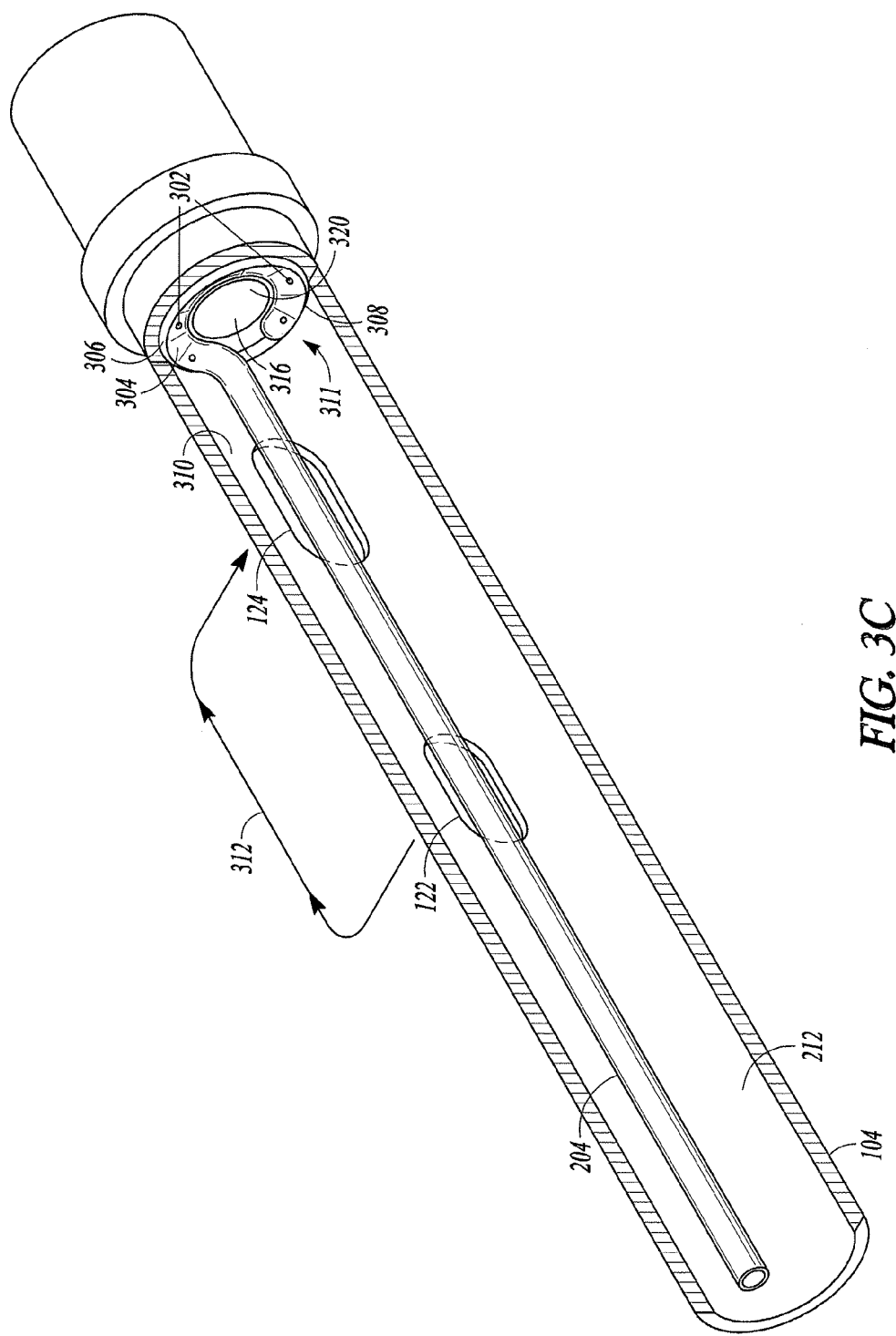
FIG. 3C is a sectional perspective view of the distal catheter portion including the fluid jet loop shown in FIG. 3A with the tapered guide surface.

Referring now to FIGS. 3A-C, the catheter distal portion 114 is shown. As previously described, the thrombectomy catheter 100 provides a cross stream flow to break up thrombus and then draw it into the catheter 100 for removal of the thrombus from the vessel. The fluid jet loop 300 shown in FIGS. 3A-C is a circular or semi-circular fixture within the catheter body 104. The fluid jet loop 300 produces fluid jets 303 (See FIGS. 3A and 3B) to create the cross stream flow 312 and thereby remove and exhaust thrombus from the vessel.

The fluid jet loop 300 extends around the catheter body interior wall 212. In one example, the fluid jet loop 300 is engaged with a catheter body interior wall 212 along a loop perimeter surface 306. As shown in FIGS. 3A-C, the fluid jet loop 300 includes fluid jet orifices 302 directed in a proximal direction toward the catheter proximal portion 112 shown in FIG. 1. Stated another way, the fluid jet orifices 302 are directed within the catheter lumen 202 along the axis of the catheter body 104 toward the catheter proximal portion 112. The fluid jet orifices generate the fluid jets 303 and correspondingly generate the cross stream flow 312. In one example, the fluid jet orifices 302 are configured to provide a jet flow velocity of between around 1 and 500 meters per second.

In the example shown in FIGS. 3A-C, the fluid jet loop 300 includes a tapered guide surface 304 (e.g., a tapered loop guide surface) forming part of the second guide portion 311 of the composite guide 128. The loop leading edge 308 of the tapered guide surface 304 is flushly engaged with an intermediate guide surface 310, for instance, the catheter body interior wall 212 shown in FIG. 3. Referring to FIGS. 3B and 3C, the tapered guide surface 304 tapers away from the intermediate guide surface 310 distally toward a fluid jet loop lumen 320 extending through the fluid jet loop 300. As shown in FIG. 3C as well as other Figures discussed herein, the tapered guide surface 304 provides a funnel-like effect that guides instruments, such as guide wires, toward the fluid jet loop lumen 320 and away from the catheter body interior wall 212. Stated another way, the tapered guide surface 304 provides a beveled transition from the catheter body interior wall 212 to the fluid jet loop lumen 320. In another alternative embodiment, not shown, tapered guide surface 304 can appear as merely a beveled ring at the distal end of the catheter without being connected to high pressure tube 204 or any other instrument. Those of skill in the art can appreciate adhesion techniques for a beveled metal ring being attached to the inside wall of a catheter such as those described herein. Stated another way, marker band 318 such as a radio-opaque marker band, or support ring 316, could all be fashioned with a beveled edge within the scope of the present disclosure to allow for smoother delivery of guide wires or other instruments.

As will be described in further detail below, the tapered guide surface 304 and the intermediate guide surface 310 form the second guide portion 311 of the composite guide 128. As described above, the composite guide 128 includes the second guide portion 311 and the first guide portion 214 shown in FIG. 2. The tapered guide surface 304 of the fluid jet loop 300 is formed with one or more techniques including, but not limited to, forming, coining, molding, casting, machining and the like. The fluid jet loop 300 is constructed with, but not limited to, metals such as stainless steel, plastics and the like.

The fluid jet loop 300, in one example, is coupled with a support ring 316 (also shown in FIGS. 3A-C). As shown in FIGS. 3A and 3B, support ring 316 extends around the catheter body interior wall 212 and is engaged with an annular shoulder 324 formed in the catheter body interior wall. The support ring 316 includes an annular groove 326 sized and shaped to receive the annular shoulder 324 and thereby hold the support ring and the fluid jet loop 300 coupled thereto in place within the catheter body 104. As further shown in FIGS. 3A and 3B, the support ring 316 includes a support ring lumen 322 in communication with the fluid jet loop lumen 320. In operation, the fluid jet loop lumen 320 is aligned with the ring lumen 322 to allow a guide wire shown with guide wire tip 328 (in FIG. 3A) to pass through the fluid jet loop 300 and the support ring 316 on the way to the guide wire orifice and the catheter distal portion 114 shown in FIG. 1. Stated another way, the tapered guide surface 304 cooperates with the intermediate guide surface 310 to funnel an guide wire or other instrument into the fluid jet loop lumen for passage through tortuous features in the catheter. In still another example, the catheter distal portion 114 further includes a marker band 318 such as a radio-opaque marker band. As shown in FIGS. 3A, B, the marker band 318 is coupled around the exterior of the catheter body 104. For instance, the marker band 318 is positioned within the recess formed by the annular shoulder 324 for the support ring 316.

The fluid jet orifices 302, as previously described, are directed toward the catheter proximal portion 112. The fluid jets 303 emanating from the fluid jet orifices 302 are thereby also directed in the proximal direction. The fluid jets 303 create a pressurized flow of fluid from the catheter distal portion 114 toward the catheter proximal portion 112 (e.g., fluid jets having a velocity of between around 1 to 500 meters per second according to the configuration of the fluid jet orifices 302 and the pressure of the fluid). As shown in FIGS. 3A, B, the fluid jets 303 create a cross stream flow 312. The cross stream flow 312 passes through the outflow orifice 122, travels outside of the catheter body 104 and returns into the catheter body 104 by way of the inflow orifice 124. In one example, the cross stream flow has a flow velocity at one or more of the inflow and outflow orifices 124, 122 that is typically within the range of the flow generated by the flow velocity from the fluid jet orifices of between around 1 to 500 meters per second, although the cross stream flow usually is lower than the maximum velocity of the flow from the jet orifices. The cross stream flow 312 thereby has a cyclical pattern that engages the pressurized fluid in the flow against the thrombus within a vessel and breaks up and removes the thrombus off of the vessel wall. The cross stream flow 312 moves the thrombus particles along with entrained fluid into the catheter body 104 through the inflow orifice 124 where the exhaust flow from the fluid jets 303 carries the particles proximally toward the catheter proximal portion and the manifold assembly 102 shown in FIG. 1. The exhausted thrombus particles are thereafter removed from the catheter 100 by way of the exhaust tube 120 (also shown in FIG. 1).

Optionally, the high pressure tube 204 extends over the inflow and outflow orifices 124, 122 and provides a virtual screen to prevent instruments, including guide wires, from wandering out of the catheter body through the orifices 124, 122. Where the high pressure tube 204 is positioned over the orifices 124, 122, the high pressure tube is part of the composite guide 128. The high pressure tube 204 cooperates with the first and second guide portions 214, 311 of the composite guide 128 to reliably guide an instrument such as a guide wire through the thrombectomy catheter 100 without snagging. Stated another way, the high pressure tube 204 positioned over the inflow and outflow orifices 124, 122 further ensures an instrument such as a guide wire is smoothly fed proximally or distally through the thrombectomy catheter 100 while minimizing snagging and wandering of the guide wire or other instrument.

Composite Guide

As discussed above, the guide insert 208 and the tapered guide surface 304 of the fluid jet loop 300 mated with the intermediate guide surface 310 form the first and second guide portions 214, 311, respectively, of a composite guide 128. The first and second guide portions 214, 311 cooperate to ensure an instrument, such as a guide wire, is reliably fed through the manifold assembly 102, the catheter body 104 and out of the catheter distal portion 114 through the guide wire orifice 126. The first and second guide portions 214 and 311 ensure an instrument such as a guide wire is fed through the thrombectomy catheter 100 consistently without engagement and snagging against features within the manifold assembly 102 and the catheter body 104.

Referring to FIG. 2, the first guide portion 214 adjacent to the manifold assembly 102 ensures that a guide wire fed into the manifold assembly 102 reliably moves through the manifold assembly 102, past the assembly cavity 206 and into the catheter lumen 202 of the catheter body 104 on its way to the catheter distal portion 114. The composite guide 128 including the first guide portion 214 and the second guide portion 311 thereby ensures reliable and consistent feeding of a guide wire (or other instrument) through the thrombectomy catheter 100 without undesirable snagging of the guide wire within the catheter 100. Optionally, the catheter body 104 and the catheter lumen 202 extending through the body foam a portion of the composite guide 128. For instance, the surfaces of the catheter body 104 defining the catheter lumen 202 provide a smooth near-featureless surface that reliably guides an instrument such as a guide wire toward the catheter distal portion 114 (if back loaded) or the catheter proximal portion 112 (if front loaded through the catheter distal portion). In still another example, the catheter lumen 202 is tapered between the catheter proximal portion 112 and the catheter distal portion 114 to further assist in guiding an instrument such as a guide wire toward the second guide portion 311 including the tapered guide surface 304 of the fluid jet loop 300.

Figure 4A:
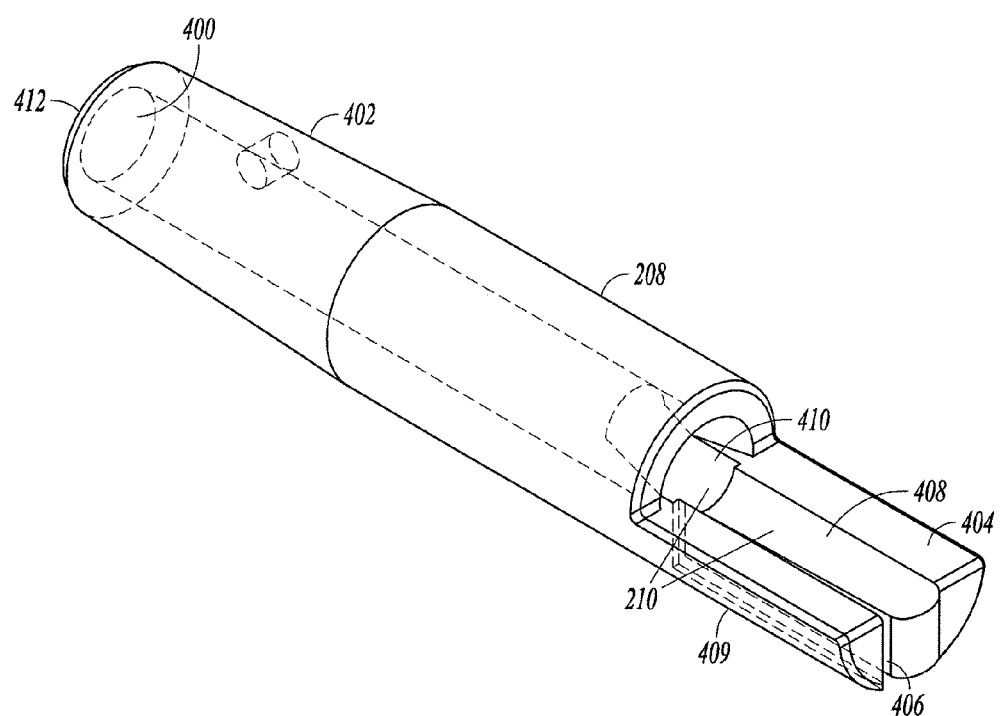
FIG. 4A is a detailed perspective view of one example of a guide insert.
Figure 4B:
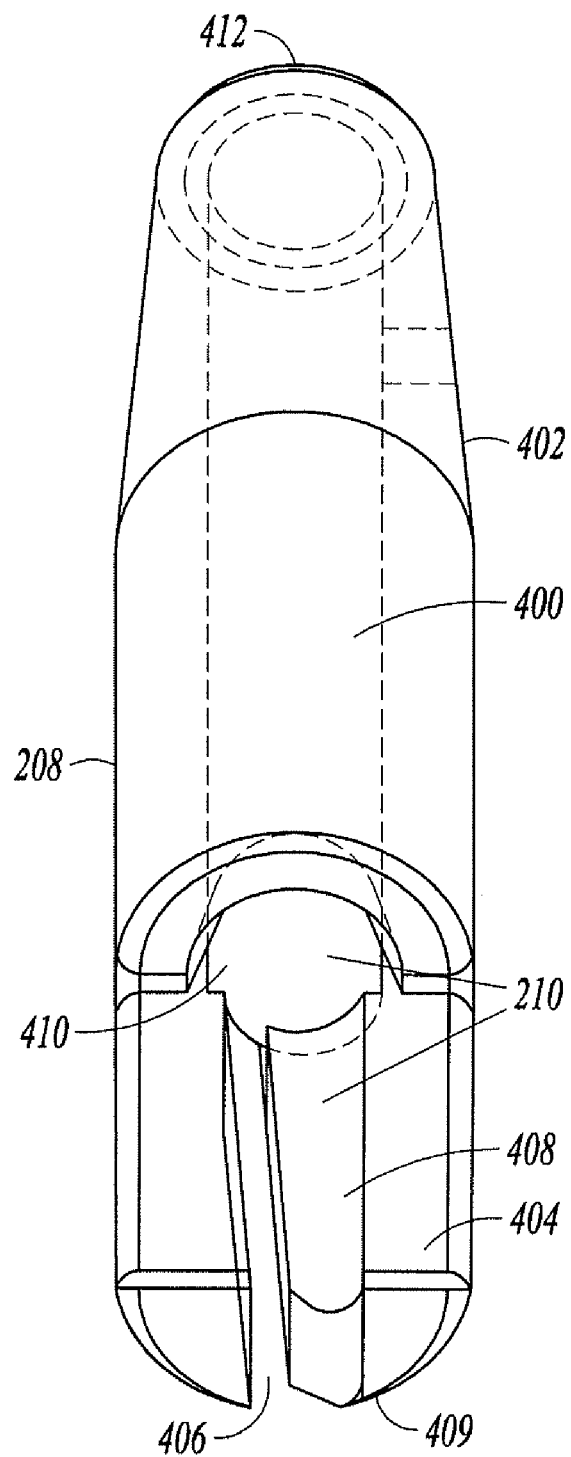
FIG. 4B is a detailed top perspective view of the guide insert shown in FIG. 4A.

Referring now to FIGS. 4A and 4B, one example of the guide insert 208 is shown. The guide insert 208 includes a guide insert lumen 400 extending through a guide insert barrel 402. The guide insert 208 further includes in the example shown a guide insert tail 404 extending away from the guide insert barrel 402. As shown in FIG. 2, the guide insert tail 404 extends within the manifold assembly 102 toward the manifold proximal portion 106 and the guide insert barrel 402 is adjacent to the manifold distal portion 108. The guide insert tail 404 shown in FIGS. 4A and 4B includes a guide insert slot 406 extending through the guide insert 208 between a guide insert groove 408 and a guide insert exterior surface 409. The high pressure tube 204 shown in FIG. 2 extends through the guide insert slot 406 and into the guide insert lumen 400. The high pressure tube 204 extends from the guide insert lumen into the catheter lumen 202. The guide insert slot 406 thereby provides an opening within the guide insert 208 to feed the high pressure tube 204 toward the catheter distal portion 114.

Referring to FIGS. 2, 4A and 4B, as previously discussed, the guide insert 208 including the guide insert surface 210 cooperates with the catheter body interior wall 212 and the manifold interior wall 201 to form a first guide portion 214 of the composite guide 128. The guide insert surface 210 provides a smooth transition to the catheter body interior wall 212 thereby allowing reliable and consistent passage of instruments such as a guide wire through the manifold assembly 102 into the guide insert 208 and through the catheter body 104 without snagging the guide wire or other instrument within the manifold assembly 102 (e.g., within the assembly cavity 206).

As shown in FIGS. 4A and 4B, the guide insert surface 210 shown in the example guide insert 208 extends across the guide insert groove 408 and into the guide insert lumen 400. Referring to FIG. 2, the catheter body 104 extends into at least a portion of the guide insert 208 and the catheter body interior wall 212 is flushly engaged with at least a portion of the guide insert surface 210. The guide insert 208 including the guide insert surface 210 provides the guiding function by filling the assembly cavity 206 (See FIG. 2) and creating a smooth transition from the manifold assembly 102 to the catheter body 104. The guide insert 208 is shaped and configured for filling of the assembly cavity 206 to ensure reliable guiding of an instrument such as a guide wire into a catheter lumen 202 from the manifold lumen 200. As shown in FIG. 2, the guide insert barrel 402 is sized and shaped to fit into a first portion of the assembly cavity 206 adjacent to the manifold distal portion 108. The guide insert tail 404 is correspondingly sized and shaped to fit within a portion of the assembly cavity 206 proximal to the first portion of the assembly cavity. For example, the guide insert tail 404 is fit within a portion of the assembly cavity 206 between the manifold lumen 200 and the exhaust tube 120 shown in FIG. 2. Stated another way, the guide insert 208 fills the assembly cavity 206 in such a way that the manifold lumen 200 is able to seamlessly communicate with the catheter lumen 202 without providing cavities or structure capable of engaging with an instrument such as a guide wire and snagging or catching the guide wire within the manifold assembly or the catheter proximal portion 112 engaged with the manifold assembly. An instrument such as a guide wire fed through the manifold lumen 200 and the catheter lumen 202 cannot wander from the lumens into cavities, including the assembly cavity 206, because of the guide insert 208. The guide insert thereby bridges across the catheter body interior wall 212 and the manifold interior wall 201 and smoothly passes an instrument such as a guide wire between the manifold assembly 102 and the catheter body 104.

Figure 5A:
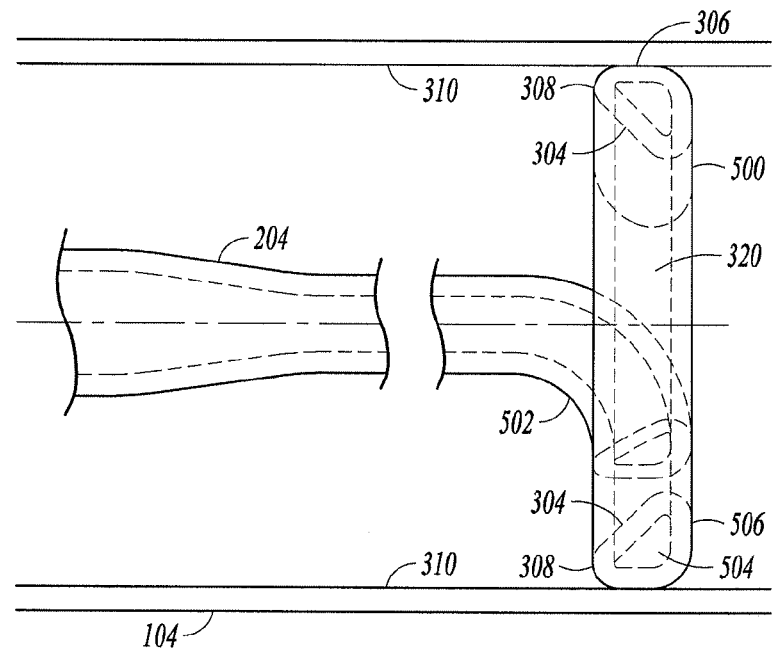
FIG. 5A is a detailed bottom view of one example of a fluid jet loop within the catheter body including a tapered guide surface.
Figure 5B:
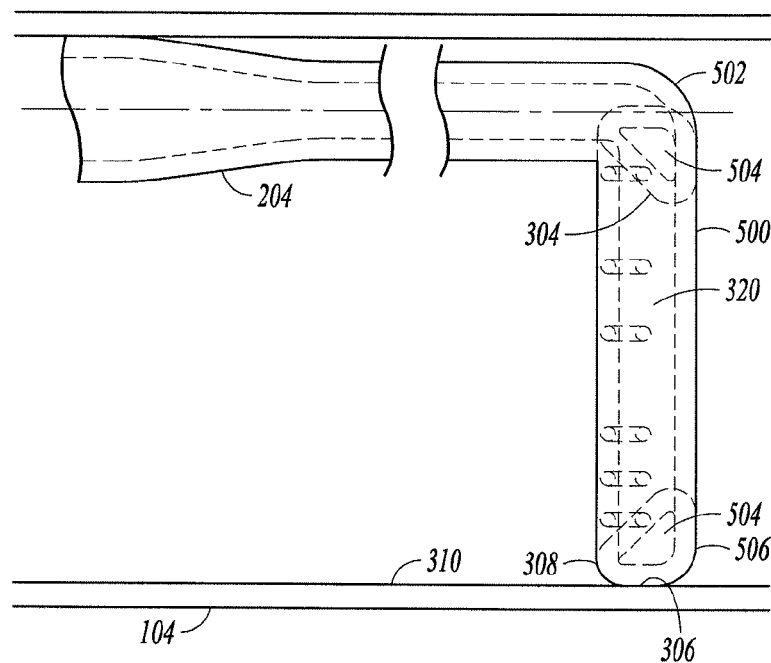
FIG. 5B is a detailed side view of the fluid jet loop shown in FIG. 5A.

FIGS. 5A and 5B show one example of a fluid jet loop 500 that forms part of the second guide portion 311 shown in FIGS. 3A, B. FIG. 5A shows a top view of the jet loop 500 within the catheter body 104. FIG. 5B shows a side view of the jet loop 500. The jet loop 500 is positionable within the catheter body 104 in an orientation that directs the fluid jet orifices 302 in the desired direction. The fluid jet loop 500 is shown in both FIGS. 5A and 5B with the high pressure tube 204 coupled to the fluid jet loop 500 with an elbow 502. The high pressure tube 204 is in communication with the interior of the fluid jet loop 500 by way of a fluid passage 504 extending around the fluid jet loop and providing high pressure fluid to each of the fluid jet orifice 302 (see FIG. 5B).

As previously discussed above, the fluid jet loop 300 includes a loop perimeter surface 306 sized and shaped for coupling with the catheter body interior wall 212 shown in FIG. 2 (e.g., intermediate guide surface 310 shown in FIGS. 3A, B). As shown in FIGS. 5A and 5B, in one example, the loop perimeter surface 306 is substantially planar and thereby engages along the intermediate guide surface 310. The fluid jet loop 500 further includes the tapered guide surface 304 including the fluid jet orifices 302. That is to say, the fluid jet orifices 302 extend through the tapered guide surface 304. As shown in FIGS. 5A and 5B, the tapered guide surface 304 extends around the entirety of the fluid jet loop 500. In another example, the tapered guide surface 304 extends over a portion of the fluid jet loop 500, for instance, an arc measuring anywhere from 0 to 360 degrees. The fluid jet loop 500 includes the fluid jet loop lumen 320 extending through the jet loop. The fluid jet loop lumen 320 is sized and shaped to pass an instrument such as a guide wire through the fluid jet loop 500 on a path to the guide wire orifice 126 shown in FIG. 1. Stated another way, the tapered guide surface 304 and the intermediate guide surface 310 cooperate to funnel a guide wire or other instrument through the fluid jet loop 300 (e.g., through fluid jet loop lumen 320). Alternatively, the fluid jet loop 320 is sized and shaped to receive a guide wire fed into the catheter body 104 through the guide wire orifice 126 (e.g., front loaded) where the guide wire is fed through the catheter proximal portion 102 shown in FIG. 1.

The tapered guide surface 304 is part of the second guide portion 311 shown in FIGS. 3A-C. For example, the tapered guide surface 304 includes a loop leading edge 308 sized and shaped for substantially flush engagement with the intermediate guide surface 310. The tapered guide surface 304 thereby provides a continuous guiding surface with the intermediate guide surface 310 to reliably and consistently direct an instrument, such as a guide wire, fed through the catheter body 104 through the fluid jet loop lumen 320 toward the guide wire orifice 126. The flush engagement between the leading edge 308 of the tapered guide surface 304 and the intermediate guide surface 310 ensures that a guide wire (shown by the guide wire tip 328 in FIG. 3A) is fed through the fluid jet lumen 320 and the support ring lumen 322. Stated another way, if the guide wire tip 328 is fed along the interior wall 212 toward the catheter distal portion 114 the guide wire tip engages with the intermediate guide surface 310 and rides from the intermediate guide surface 310 over the tapered guide surface 304 (including the fluid jet orifices 302) because of the flush engagement between the loop leading edge 308 and the intermediate guide surface 310. The smooth transition between tapered guide surface 304 (appearing as a funnel-like surface in FIG. 3C) and intermediate guide surface 310 serves to funnel instruments such as guide wires through convoluted features within the catheter (e.g., the fluid jet loop and the support ring 316) and forms the second guide portion. The guide wire tip 328 is then fed into the fluid jet loop lumen 320 and the support ring 322 where it then moves toward the guide wire orifice 126 and extends out of the catheter 100 into the vessel as desired.

In the example shown at FIGS. 5A and 5B, the fluid jet loop 500 further includes a distal loop surface 506. The distal loop surface 506 is substantially orthogonal to the catheter body interior wall 212 shown in FIG. 2. The orthogonal distal loop surface 506 allows for easy coupling with a structure such as the support ring 316 shown in FIGS. 3A, B and further described in FIGS. 6A and 6B. In yet another example, the distal loop surface 506 includes a tapered surface similar to the tapered guide surface 304. In such an example the distal loop surface 506 includes a leading edge substantially flush with the catheter body interior wall 212 (e.g., the intermediate guide surface 310). A distal loop surface 506 would then taper toward the fluid jet loop lumen 320 and the distal loop surface 506 would thereby have a taper oriented at an angle opposed to the angle of the tapered guide surface 304. Stated another way, the fluid jet loop lumen 500 with the tapered distal loop surface 506 includes a tapered guide surface 304 tapering from the proximal portion of the catheter body 104 toward the catheter distal portion 114 and a distal loop surface 506 tapering from the catheter distal portion 114 toward the catheter proximal portion 112. Including tapered surfaces on the tapered guide surface 304 and the distal loop surface 506 allows for back loading (insertion of a guide wire or other instrument through the manifold assembly 102 toward the catheter distal portion 114) and front loading of instruments such as a guide wire or flow wire and the like (through the guide wire orifice 126 toward the manifold assembly 102) thereby providing additional flexibility for use of the catheter 100 (FIG. 1). The ability to front load and back load an instrument in the catheter 100 provides enhanced utility for an operator and eliminates the need to exchange catheters during a procedure.

Figure 6A:
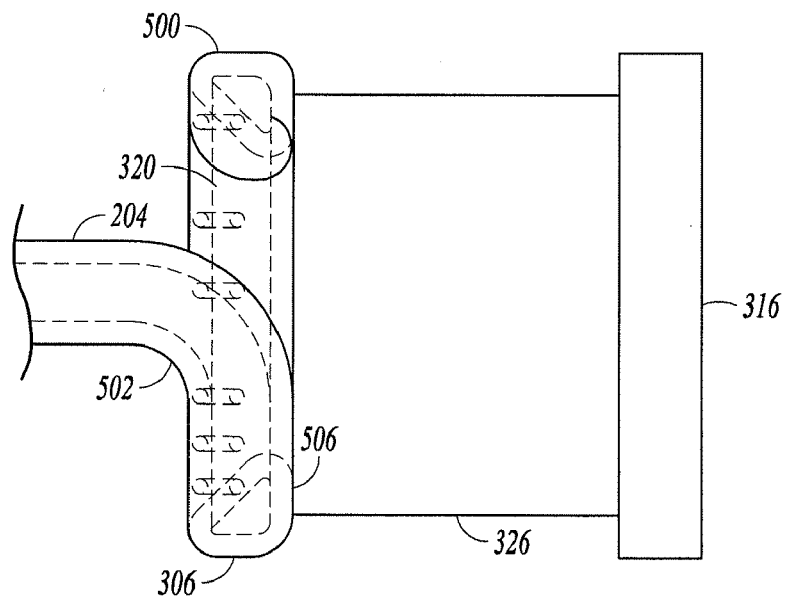
FIG. 6A is a detailed bottom view of another example of a fluid jet loop including a tapered guide surface coupled with a support ring.
Figure 6B:
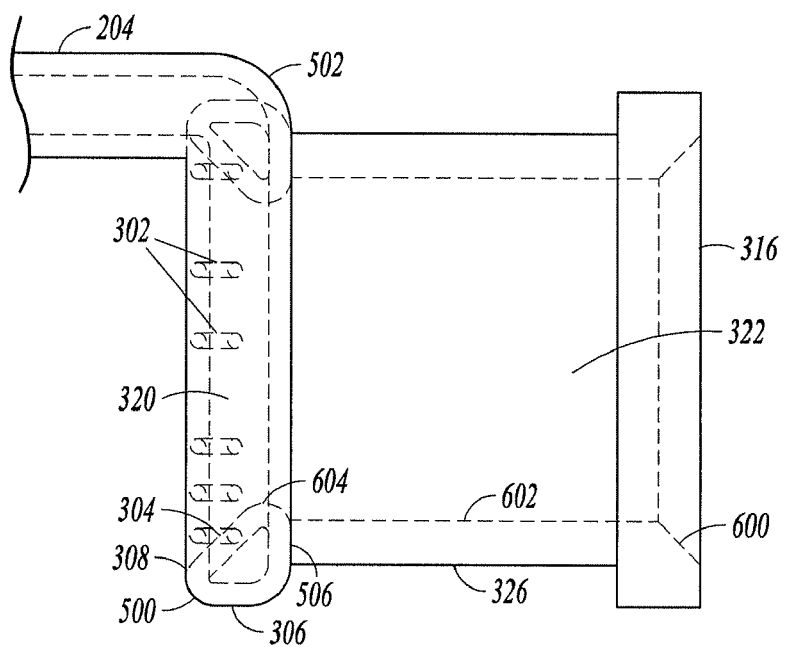
FIG. 6B is a detailed side view of the fluid jet loop and support ring shown in FIG. 6A.

FIGS. 6A and 6B show the fluid jet loop 500 coupled with the support ring 316. In one example, the fluid jet loop 500 is coupled with the support ring 316 by way of a weld. The fluid jet loop 500 is optionally coupled with support ring 316 with one or more of a variety of features including but not limited to mechanical interference fittings, mechanical couplings, adhesives, molding and the like. The fluid jet loop 500 shown in FIGS. 6A and 6B includes at least some of the features shown in FIG. 3, FIGS. 5A and 5B. For instance, the fluid jet loop 500 includes a tapered guide surface 304 including the fluid jet orifices 302 configured to direct fluid jets toward a catheter proximal portion 112. The fluid jet loop 500 further includes a loop leading edge 308 sized and shaped for flush coupling with the intermediate guide surface 310 (e.g., the catheter body interior wall 212).

As previously described, the support ring 316 includes a support ring lumen 322 extending through the support ring. As shown in FIG. 6B, the support ring lumen 322 is circumscribed by a distal support ring tapered surface 600 and a support ring inner wall 602. The support ring 322 includes an annular groove 326 sized and shaped to allow the support ring 322 to couple with the annular shoulder 324 of the catheter body 104 (FIGS. 3A, B). As shown in FIGS. 6A and 6B the annular groove 326 is positioned between the fluid jet loop 500 having the tapered guide surface 304 and the distal support ring tapered surface 600. The support ring inner wall 602 extends over the annular groove 326.

The distal support ring tapered surface 600 allows for front loading of an instrument, such as a guide wire, through the guide wire orifice 126 shown in FIG. 1. A front loaded instrument such as a guide wire is inserted into the catheter body near the catheter distal portion 114 (e.g., through the guide wire orifice 126) and fed toward the manifold assembly 102. As shown in FIG. 6B, the support ring inner wall 602 is substantially flush with a loop trailing edge 604. Where the fluid jet loop 500 flushly transitions from the loop trailing edge 604 to the support ring inner wall 602 a continuous guide surface is provided between the fluid jet loop 500 and the support ring 322 thereby allowing reliable and consistent delivery of instruments through the fluid jet loop 500 and support ring 322. Snagging of instruments (e.g., guide wires having curved tips) within the support ring 322 and fluid jet loop 500 is thereby avoided because of the flush engagement between the support ring inner wall 602 and the loop trailing edge 604. Stated another way, the distal support ring tapered surface 600 and the tapered guide surface 304 funnel instruments such as guide wires and the like—whether back loaded or front loaded—through the catheter and substantially prevent snagging of the instruments on features within the catheter. Provision of the distal support ring tapered surface 600 together with the tapered guide surface 304 of the fluid jet loop 500 thereby facilitates front loading and back loading of an instrument such as a guide wire through the catheter body 104.

Figure 7:
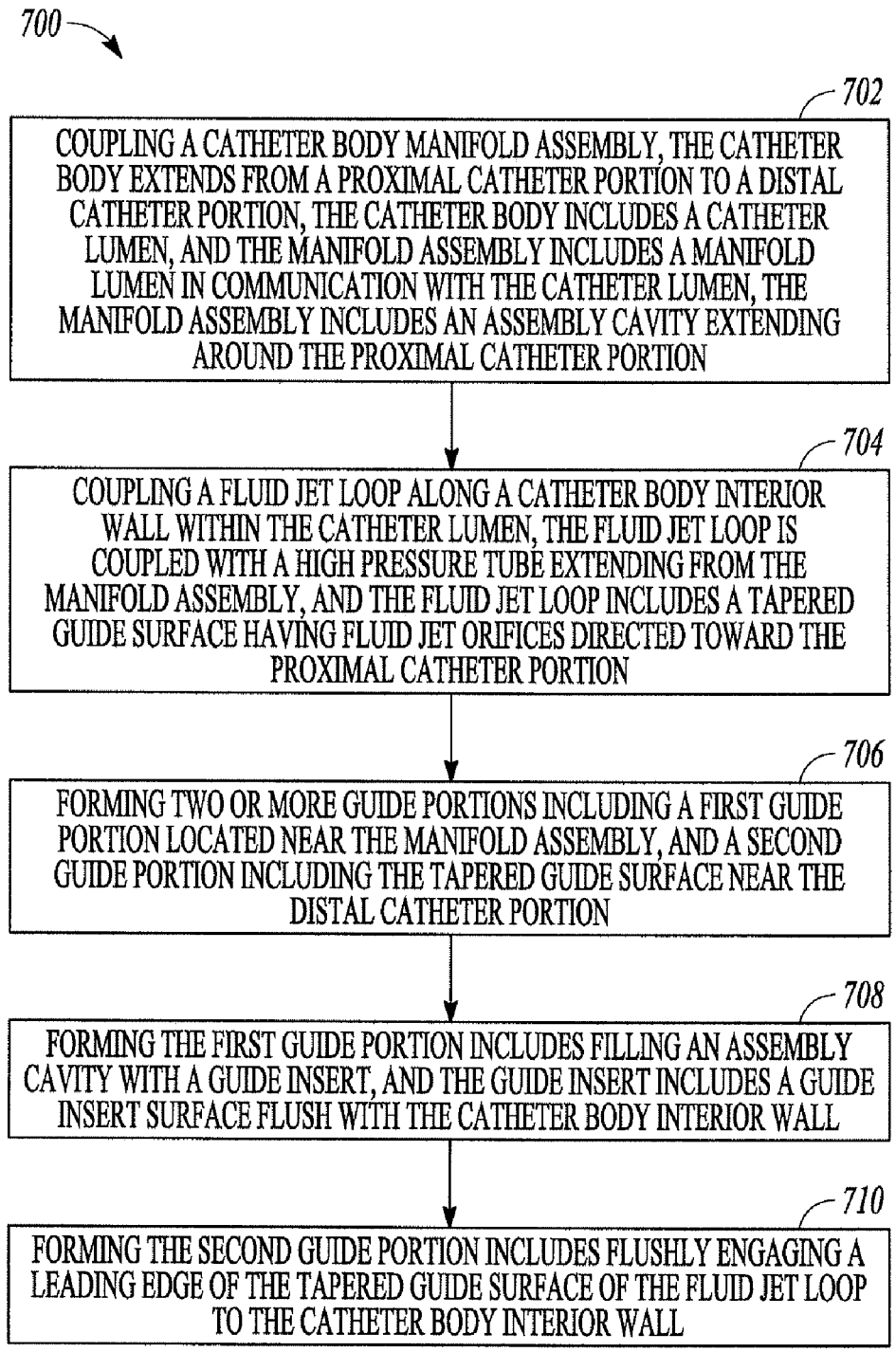
FIG. 7 is a block diagram showing one example of a method for making a thrombectomy catheter including a composite guide.

Referring now to FIG. 7, one example of a method 700 for making a thrombectomy catheter is shown. Reference is made to components previously described in FIGS. 1 through 6B. While reference is made to one or more similar components it is implicit that other similar components and their equivalents are also included in the description of the method 700. The method 700 includes at 702 coupling a catheter body, such as catheter body 104, with a manifold assembly 102 (see FIG. 1). The catheter body 104 extends from a proximal catheter portion 112 to a distal catheter portion 114. The catheter body 104 further includes a catheter lumen 202 (See FIG. 2). The manifold assembly 102 includes a manifold lumen 200 (Also shown in FIG. 2). The catheter lumen 202 and manifold lumen 200 are in communication. The manifold assembly 120 further includes an assembly cavity, such as cavity 206 shown in FIG. 2. As shown in FIG. 2, the assembly cavity 206 extends around the catheter proximal portion 112. The assembly cavity 206 assists in assembly of the thrombectomy catheter 100. For instance, the high pressure tube 204 (FIG. 2) and the fluid jet loop 300 (FIGS. 3A, B) are fed through the exhaust tube coupled with the manifold assembly 102 and into the catheter body 104 for assembly.

At 704, a fluid jet loop, such as fluid jet loop 300, is coupled along a catheter body interior wall 212. The catheter body interior wall defines the catheter lumen 202. The fluid jet loop 300 is coupled with a high pressure tube 204 extending from the manifold assembly 102. The fluid jet loop 300 includes a tapered guide surface 304 having fluid jet orifices 302. As shown in FIGS. 3A-C, the fluid jet orifices are directed toward the proximal catheter portion 112 of the catheter body 104.

The method 700 further includes at 706, forming two or more guide portions such as a first guide portion 214 and a second guide portion 311 of a composite guide 128. The first guide portion 214 is located near the manifold assembly 102 and the second guide portion 311 includes the tapered guide surface 304 near the distal catheter portion 114. As previously described, the tapered guide surface 304 is part of the fluid jet loop 300 shown in FIGS. 3A-C.

At 708, forming the first guide portion 214 includes filling the assembly cavity 206 with a guide insert 208. The guide insert 208 fills the assembly cavity 206 and includes a guide insert surface 210 flush with the catheter body interior wall. Referring to FIG. 2, the guide insert surface 210 is flush and adjacent to the catheter body interior wall 212 and thereby provides a smooth and consistent transition from the manifold assembly 102 to the guide insert 208, and from the guide insert 208 to the catheter body 104.

At 710, the second guide portion 311 of the composite guide 128 is formed including flushly engaging a leading edge 308 of the tapered guide surface 304 of the fluid jet loop 300 to the catheter body interior wall 212. In another example, the leading edge 308 of the tapered guide surface 304 is flushly engaged with an intermediate guide surface 310. Optionally, the intermediate guide surface 310 includes the catheter body interior wall 212. In yet another option, the intermediate guide surface 310 includes a supplemental feature of the catheter body 104, for instance, a surface extending through and over a portion of the catheter body 104.

Several options for the method 700 of making the thrombectomy catheter 100 follow. In one example, filling the assembly cavity 206 with the guide insert 208 includes positioning a guide insert barrel 402 around the proximal catheter portion 112. In another example, filling the assembly cavity 206 with the guide insert 208 includes positioning a guide insert tail 404 (see FIG. 4) over the interface between the exhaust tube 120 and the manifold lumen 200. As previously described, the guide insert tail 404 includes a guide insert slot 406 sized and shaped to allow the high pressure tube 204 to extend through the exhaust tube 120 into the manifold lumen 200 and the catheter lumen 202. Further, the guide insert slot 406 of the guide insert tail 404 allows for communication between the catheter lumen 202, the manifold lumen 200 and the injection port 118 extending away from the manifold assembly 102. Exhaust from operation of the thrombectomy catheter moved through the guide insert slot 406 from the catheter lumen 202 and manifold lumen 200 into the exhaust tube 120. The guide insert slot 406 is thereby able to pass fluids including fluids having entrained thrombus to an exhaust tube and further allows the high pressure tube to extend from the exhaust tube 120 into the catheter lumen 202 while at the same time reliably guiding an instrument such as a guide wire into the catheter lumen 202 from the manifold lumen 200. Further, the guide insert 208 substantially prevents wandering of an instrument, such as a guide wire, out of the manifold lumen 200 and into cavities (e.g., the assembly cavity 206) within the manifold 102. In yet another example, the method 700 further includes feeding the fluid jet loop 300 and the high pressure tube 204 through the assembly cavity 206 and the exhaust tube 120 in the manifold assembly 102 prior to filling the assembly cavity 206 with the guide insert 208. Stated another way, the assembly cavity 206 provides additional space in the manifold 102 for facilitating positioning of the high pressure tube 204 and the fluid jet loop 300 within the catheter body 104. The additional space allows the high pressure tube 204 and fluid jet loop 300 to easily navigate through the exhaust tube 120 and bend within the manifold assembly 102 to enter the catheter lumen 202. After positioning of the fluid jet loop 300 and high pressure tube 204 the guide insert 208 is positioned within the assembly cavity 206 to fill the assembly cavity and provide the first guide portion 214 between the manifold lumen 200 and the catheter lumen 202.

FIG. 8 shows one example of a method 800 for using a catheter such as the thrombectomy catheter 100 shown in FIG. 1. Method 800 refers to elements shown in FIGS. 1 through 6B. The references are exemplary and implicitly include any alternative elements described and their equivalents. At 802, an instrument, such as a guide wire, is fed into the catheter 100. The guide wire tip 328 is shown, for example, in FIG. 3A. The catheter includes a manifold assembly 102 coupled with a catheter body 104 at a proximal catheter portion 112. A catheter lumen 202 extends through the catheter body 104 from the proximal catheter portion 112 to a distal catheter portion 114. An assembly cavity 206 extends around the proximal catheter portion 112 within the manifold assembly 102.

At 804, the instrument (e.g., a guide wire) is fed through at least the catheter lumen 202 and a fluid jet loop 300 near a catheter distal portion 114. The instrument is fed into and through the catheter lumen 202 by way of a composite guide surface including, for example, a first guide portion 214 and a second guide portion 311. Feeding the instrument includes guiding the instrument into a catheter lumen through a guide insert 208 and guiding the instrument over an intermediate guide surface flushly engaged with a tapered guide surface 304 of the fluid jet loop 300.

At 806, the method 800 includes guiding the instrument into the catheter lumen 202 through the guide insert 208 filling the assembly cavity 206. The instrument is guided along a guide insert surface 210 flush with the catheter body interior wall 212. As previously described, the flush transition made by the guide insert surface 210 to the catheter lumen 202 from the manifold lumen 200 substantially prevents wandering of the instrument outside of the manifold lumen and the catheter lumen, for instance, into the assembly cavity 206. The instrument is thereby reliably fed out of the manifold assembly 102 and into the catheter lumen 202 without lodging within spaces within the assembly cavity 206 otherwise present for assembly purposes of the thrombectomy catheter 100.

The method 800 further includes at 808, guiding the instrument, for instance the guide wire shown by the guide wire tip 328 in FIG. 3A, along a distal guide such as the second guide portion 311 near the distal catheter portion 114. The distal guide includes an intermediate guide surface 310 and a tapered guide surface 304 of the fluid jet loop 300. The tapered guide surface includes fluid jet orifices 302 directed toward the proximal catheter portion 112, as described above. As shown in FIG. 3A, the instrument 328 is guided along the intermediate guide surface 310 through first, second, and third guide wire positions to illustrate the guide function of the second guide portion 311. At 330, a first exemplary guide wire position, guide wire tip 328 is positioned proximally relative to the fluid jet loop 300 and is moved distally along the intermediate guide surface 310. At 332, in a second exemplary guide wire position, guide wire tip 328 is moved past the outflow orifice 122 and is adjacent to the fluid jet loop 300. In a third exemplary guide wire position 334, guide wire tip 328 is guided through the fluid jet loop lumen 320 by the second guide portion 311. The intermediate guide surface 310 is flushly engaged with a loop leading edge 308. Guide wire tip 328 rides along the continuous surface created by the intermediate guide surface 310 and the tapered guide surface 304 to funnel guide wire tip 328 through the fluid jet loop lumen 320 of the fluid jet loop 300. Snagging of the guide wire, including a curved guide wire having a non-linear bent or hooked distal shape, is reliably avoided because of the continuous guide surface of the second guide portion 311 of the composite guide 128.

Several options for the method 800 follow. In one example, feeding the instrument through at least the catheter lumen 202 and the fluid jet lumen 300 includes the front loading of the instrument through a distal guide wire orifice such as guide wire orifice 126 shown in FIG. 1. Feeding the instrument through the catheter lumen 202 and the fluid jet loop 300 further includes back loading of the instrument through the manifold assembly 102. Stated another way, the instrument is fed through the introducer 116 positioned at the proximal portion of the manifold assembly 102. From there the instrument is fed into the manifold lumen 200 of the manifold assembly 202. In yet another option, where the instrument is front loaded through the guide wire orifice 126 the guide wire tip, such as guide wire tip 328 is fed over a distal support ring tapered surface 600 shown in FIGS. 6A and 6B. The distal support ring tapered surface 600 acts in a similar manner to the tapered guide surface 304 of the fluid jet loop 300 and funnels the guide wire tip through the support ring. The guide wire tip 328 is thereafter fed over the support ring inner wall 602, and the support ring inner wall 602 is substantially flush with the fluid jet loop 300 to guide the front loaded instrument into the catheter lumen 202 for passage through the catheter lumen to the manifold assembly 102. The ability to back load and front load instruments increases the utility of the thrombectomy catheter 100 because the user does not need to exchange catheters during a procedure.

The catheter and methods described above and shown in the figures provide a catheter assembly capable of using a single lumen to provide thrombectomy therapy to a desired treatment site while also able to smoothly navigate a guide wire or other instrument through the same lumen containing the thrombectomy apparatus. By including a composite guide in the distal catheter portion and at the interface between the manifold assembly and the catheter body instruments including guide wires, are fed—without snagging on obstructions—through the manifold assembly and the catheter body and out of an orifice in the distal catheter portion. Guide wires, including guide wires having a variety of shapes and bends, that are otherwise prone to snagging within a catheter body are readily fed through the catheter body including the composite guide. A composite guide including the first and second guide portions is thereby able to facilitate consistent and reliable navigation of a guide wire through the catheter body.

An assembly cavity is provided within the manifold assembly to facilitate assembly of the catheter. For instance, the high pressure tube and the fluid jet loop are fed through the assembly cavity to position the high pressure tube and the fluid jet loop within the catheter body. The guide insert is positioned within the manifold assembly and fills the assembly cavity after the high pressure tube and the fluid jet loop are positioned. The catheter body is fed into the guide insert and creates a substantially flush engagement and transition between the catheter lumen and the manifold lumen. The guide insert forms a first guide portion of the composite guide. Instruments are reliably fed from the manifold into the catheter body without wandering into spaces including the assembly cavity. Stated another way, the guide insert fills the assembly cavity and substantially eliminates any cavities for the guide wire to snag within as it is fed through the manifold assembly toward the catheter body distal portion. In a similar manner the first guide portion guides an instrument front loaded (in contrast to back loading) through the catheter body into the manifold assembly. The capability to front load and back load an instrument minimizes the need to exchange a catheter able to perform front loading or back loading for another catheter capable of performing the other form of loading (i.e., back or front loading).

The second guide portion of the composite guide directs an instrument, such as a guide wire, through the catheter body and toward the distal catheter portion. The intermediate guide surface (e.g., the catheter body interior wall) flushly engages with the leading edge of the tapered guide surface of the fluid jet loop. As the guide wire is fed through the catheter lumen the guide wire slides along the intermediate guide surface and slides over the continuous surface created by the tapered guide surface mated to the intermediate guide surface. The guide wire tip engages against the tapered guide surface of the fluid jet loop and rides over the tapered guide surface into the fluid jet loop lumen and toward the guide wire orifice of the catheter. The intermediate guide surface and the tapered guide surface of the fluid jet loop thereby cooperate to form the second guide portion and funnel the instrument through the fluid jet loop. In another example, where the fluid jet loop is coupled with a support ring the support ring includes a tapered surface at its distal end that tapers toward a support ring inner surface that is substantially flush with a trailing edge of the fluid jet loop tapered guide surface. Front loading of the guide wire, for instance, through the guide wire orifice is performed in a similar manner to the back loading method previously described. For instance, the guide wire is fed over the support ring tapered guide surface into the support ring and through the fluid jet loop lumen toward the manifold assembly. The second guide portion of the composite guide (e.g., the guide insert) provides a continuous smooth transition from the catheter body into the manifold assembly to feed the guide wire into the manifold assembly.

The composite guide including the first and second guide portions is thereby able to guide an instrument through the catheter body containing elements and features necessary for thrombectomy action including, for example, a high pressure tube, a fluid jet loop, inflow and outflow orifices, a support ring and the like. By providing the composite guide a guide wire is able to smoothly pass through the catheter lumen consistently and reliably without snagging on features within the catheter lumen. Further, the catheter is able to perform a thrombectomy procedure and guide the instrument through the same lumen used for the procedure. Stated another way, the thrombectomy catheter and methods described herein provide a catheter with a single lumen and composite guide that consolidates operation of a thrombectomy system with delivery of an instrument to a desired treatment site.

Although the present disclosure has been described in reference to preferred embodiments, persons skilled in the art will recognize that changes may be made in form and detail without departing from the spirit and scope of the disclosure. It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present application. The scope of the present disclosure should, therefore, be determined with reference to the appended claims, along with the full scope of equivalents to which such claims are entitled.

What is claimed is:

1. A catheter comprising:
 a catheter body with a catheter lumen extending from a proximal catheter portion to a distal catheter portion, the catheter body including a catheter body interior wall having an intermediate guide surface, and the catheter lumen extends along the catheter body interior wall;
 a manifold assembly coupled with the proximal catheter portion, a manifold lumen extends through the manifold assembly from a proximal manifold portion to a distal manifold portion, the manifold lumen is in communication with the catheter lumen, and the manifold lumen includes an assembly cavity extending around the proximal catheter portion;
 a fluid jet loop having a loop perimeter surface adjacent to the intermediate guide surface and being coupled with a high pressure tube at the distal catheter portion, the fluid jet loop extends around the loop perimeter surface to form a fluid jet loop lumen, the fluid jet loop includes fluid jet orifices along a tapered loop guide surface, and the tapered loop guide surface tapers continuously both inwardly and distally from the intermediate guide surface of the catheter body interior wall and the loop perimeter surface toward a fluid jet loop inner perimeter and the fluid jet loop lumen; and
 a composite guide including:
  a proximal guide insert positioned within the assembly cavity, the proximal guide insert includes a guide insert surface substantially flush with the catheter body interior wall, and the proximal guide insert is configured to guide an instrument past the assembly cavity and into the catheter lumen, and
  a distal guide including the tapered loop guide surface and the intermediate guide surface of the catheter lumen flushly engaged with a leading edge of the tapered loop guide surface, the distal guide continuously tapering inwardly and distally along at least the tapered loop guide surface from the intermediate guide surface of the catheter body interior wall, wherein the distal guide is configured to guide the instrument over the intermediate guide surface, the tapered loop guide surface and through the fluid jet loop.

2. The catheter of claim 1, wherein the tapered guide surface tapers inwardly and distally away from the intermediate guide surface toward the fluid jet loop lumen.

3. The catheter of claim 1, wherein the fluid jet loop includes a distal loop guide surface, and the distal loop guide surface tapers inwardly from a distal edge flushly engaged with the intermediate guide surface toward the fluid jet loop lumen.

4. The catheter of claim 1, further comprising a support ring coupled with the fluid jet loop, and the support ring includes a support ring lumen in communication with the fluid jet loop lumen.

5. The catheter of claim 1, wherein the catheter body includes one or more inflow and outflow orifices extending from the catheter lumen to a catheter exterior near a catheter distal portion, and the one or more inflow orifices are positioned between the one or more outflow orifices and the fluid jet loop.

6. The catheter of claim 5, wherein one or more of the inflow and outflow orifices are configured to receive a fluid flow over the catheter exterior of around 1 to 500 meters per second, and the fluid flow at least extends from one or more of the outflow orifices to one or more of the inflow orifices.

7. A method of using a catheter comprising:
  feeding an instrument into the catheter, the catheter includes a manifold assembly coupled with a catheter body at a proximal catheter portion, a catheter lumen extends through the catheter from the proximal catheter portion to a distal catheter portion, the catheter body including a catheter body interior wall having an intermediate guide surface, the catheter lumen extends along the catheter body interior wall, and an assembly cavity extends around the proximal catheter portion; and
  feeding the instrument through at least a catheter lumen and a fluid jet loop, and the instrument is fed into and through the catheter lumen by way of a composite guide surface, wherein feeding the instrument includes:
    guiding the instrument into the catheter lumen through a guide insert filling the assembly cavity, and the instrument is guided along a guide insert surface in a proximal guide insert flush with a catheter body interior wall, and
    guiding the instrument along a distal guide near the distal catheter portion, wherein the distal guide includes the intermediate guide surface and a tapered guide surface of the fluid jet loop tapering continuously both inwardly and distally from the intermediate guide surface of the catheter body interior wall and a fluid jet loop outer perimeter to a fluid jet loop inner perimeter, and the tapered guide surface includes fluid jet orifices, and the instrument is guided along the tapered guide surface and the intermediate guide surface flushly engaged with a leading edge of the tapered guide surface.

8. The method of using a catheter of claim 7, wherein feeding the instrument through at least the catheter lumen and the fluid jet loop includes front loading of the instrument through a distal guide wire orifice in the catheter body and back loading of the instrument through the manifold assembly.

* * * * *